(12) United States Patent
Lee-Chen et al.

(10) Patent No.: US 10,716,768 B2
(45) Date of Patent: Jul. 21, 2020

(54) METHOD FOR TREATING ABNORMAL B-AMYLOID AGGREGATION MEDIATED DISEASES

(71) Applicant: NATIONAL TAIWAN NORMAL UNIVERSITY, Taipei (TW)

(72) Inventors: Guey-Jen Lee-Chen, Taipei (TW); Wenwei Lin, Taipei (TW)

(73) Assignee: NATIONAL TAIWAN NORMAL UNIVERSITY, Taipei (TW)

( * ) Notice: Subject to any disclaimer, the term of this patent is extended or adjusted under 35 U.S.C. 154(b) by 0 days.

(21) Appl. No.: 15/655,967

(22) Filed: Jul. 21, 2017

(65) Prior Publication Data

US 2018/0042864 A1 Feb. 15, 2018

(30) Foreign Application Priority Data

Aug. 11, 2016 (TW) .............. 105125668 A (51) Int. Cl.
*A61K 31/37* (2006.01)
*A61K 31/12* (2006.01)
(52) U.S. Cl.
CPC .............. *A61K 31/12* (2013.01); *A61K 31/37* (2013.01)
(58) Field of Classification Search
None
See application file for complete search history.

(56) References Cited

FOREIGN PATENT DOCUMENTS

CA        2401452 A1 * 3/2003    ........... A61K 31/352

OTHER PUBLICATIONS

Yang et al. "Curcumin Inhibits Formation of Amyloid Beta Oligomers and Fibrils, Binds Plaques, and Reduces Amyloid in Vivo". Journal of Biological Chemistry. 2005; 280(7):5892-5901. (Year: 2005).*

Hamdi et al. "A Rapid Access to New Coumarinyl Chalcone and Substituted Chromeno[4,3-c]Pyrazol-4(1H)-Ones and Their Antibacterial and DPPH Radical Scavenging Activities". Med Chem Res. 2011; 20:522-530. (Year: 2011).*
Huang et al. "Role of Oxidative Stress in Alzheimer's Disease (Review)". Biomedical Reports. Mar. 2016; 4:519-522. (Year: 2016).*
Vazquez-Rodriguez et al. "Synthesis of Coumarin-Chalcone Hybrids and Evaluation of Their Antioxidant and Trypanocidal Properties". Med Chem Commun. 2013; 4:993-1000. (Year: 2013).*
Perez-Cruz et al. "Synthesis and Electrochemical and Biological Studies of Novel Coumarin-Chalcone Hybrid Compounds". Journal of Medicinal Chemistry. 2013, 56:6136-6145. (Year: 2013).*
Robert A. Orlando et al., "A Chemical Analog of Curcumin as an Improved Inhibitor of Amyloid Abeta Oligomerization", Mar. 19, 2012, vol. 7, Issue 3, pp. 1-8.
Marina Y. Fosso et al., "Differential Effects of Structural Modifications on the Competition of Chalcones for the PIB Amyloid Imaging Ligand-Binding Site in Alzheimer's Disease Brain and Synthetic Aβ Fibrils", ACS Chemical Neuroscience, 2016, 7 (2), pp. 171-176.
Emily Hofmann et al., "Hydroxylated chalcones with dual properties: Xanthine oxidase inhibitors and radical scavengers", vol. 24, Issue 4, Feb. 15, 2016, pp. 578-587.

* cited by examiner

*Primary Examiner* — Leslie A. Royds Draper
(74) *Attorney, Agent, or Firm* — Bacon & Thomas, PLLC (57) ABSTRACT

The present invention provides a use of a compound to prepare a pharmaceutical composition for treating abnormal β-amyloid aggregation mediated diseases. The compound is represented by the following formula (I):

wherein A, B, $R_1$, $R_2$, $R_3$, $R_4$, $R_5$ and $R_6$ are defined in the specification.

7 Claims, 11 Drawing Sheets

METHOD FOR TREATING ABNORMAL β-AMYLOID AGGREGATION MEDIATED DISEASES

CROSS REFERENCE TO RELATED APPLICATION

This application claims the benefits of the Taiwan Patent Application Serial Number 105125668, filed on Aug. 11, 2016, the subject matter of which is incorporated herein by reference.

BACKGROUND OF THE INVENTION

1. Field of the Invention

The present disclosure relates to a method for treating abnormal β-amyloid (Aβ) aggregation mediated diseases with a pharmaceutical composition.

2. Description of Related Art

Abnormal protein aggregation or inclusion is present in most age-related neurodegenerative diseases, wherein abnormal β-amyloid (Aβ) aggregation is the most common abnormal protein aggregation. Furthermore, abnormal β-amyloid aggregation causes Alzheimer's disease (AD). Alzheimer's disease is the most well-known form of dementia and it causes memory loss and progressive cognitive decline. However, there is no drug for curing Alzheimer's disease at the moment, and the existing treatments for AD can merely preserve or improve cognitive function and reduce behavioral disorders to delay disease progression. As a result, there is an urgent need to find methods for treating or delaying Alzheimer's disease.

Pathological features of Alzheimer's disease include extracellular amyloid and intracellular neurofibrillary tangle, wherein the main component of extracellular amyloid is β-amyloid. Furthermore, β-amyloid deposition increases oxidative stress and thus leads to death of nerve cells. Hence, the level of deposition is strongly relevant to neurotoxicity. Therefore, it is desirable to provide a compound to inhibit abnormal β-amyloid aggregation, and the compound can be used to treat or effectively delay neurodegenerative diseases related to abnormal β-amyloid aggregation such as Alzheimer's disease.

SUMMARY OF THE INVENTION

The object of the present disclosure is to provide a method for inhibiting abnormal β-amyloid aggregation mediated diseases in order to treat or effectively delay neurodegenerative diseases related to abnormal β-amyloid aggregation, for example, Alzheimer's disease.

More specifically, the object of the present disclosure is to provide a method for inhibiting abnormal β-amyloid aggregation, reducing reactive oxygen species (ROS) content, promoting neurite outgrowth in order to treat or effectively delay disease progression, such as neurodegenerative diseases related to abnormal β-amyloid aggregation, for example, Alzheimer's disease.

To achieve the object, the method for treating an abnormal β-amyloid aggregation mediated disease of the present disclosure comprises: administering a pharmaceutical composition comprising a compound represented by the following formula (I), wherein A is H, —OH or O, and B is H or C=O; when A and B are not bonded, A is H or —OH, and B is H; or when A and B are bonded to form a ring, A is O, and B is C=O; and each $R_1$, $R_2$, $R_3$, $R_4$ and $R_6$ is independently selected from the group consisting of H, —OH, —$OR_7$, and halogen; $R_7$ is C1-C5 alkyl, and $R_5$ is a substituted or unsubstituted phenyl or C2-C5 alkenyl.

In addition, the method for inhibiting β-amyloid aggregation in a subject comprises: administering a pharmaceutical composition comprising a compound represented by the following formula (I) to a subject, wherein A is H, —OH or O, and B is H or C=O; when A and B are not bonded, A is H or —OH and B is H; or when A and B are bonded to form a ring, then A is O, and B is C=O; and each $R_1$, $R_2$, $R_3$, $R_4$ and $R_6$ is independently selected from the group consisting of H, —OH, —$OR_7$, and halogen; $R_7$ is C1-C5 alkyl, and $R_5$ is a substituted or unsubstituted phenyl or C2-C5 alkenyl.

The method as provided in the present disclosure, wherein each $R_1$, $R_2$, $R_3$, $R_4$ and $R_6$ of formula (I) can be independently selected from the group consisting of H, —OH, —O—$CH_3$, and Br. $R_5$ of formula (I) can be phenyl substituted with —OH or —$OR_8$, and $R_8$ is C1-C5 alkyl, preferably, $R_5$ of formula (I) can be phenyl substituted with —OH or —O—$CH_3$. $R_5$ of formula (I) can be C2-C5 alkyl substituted with phenyl, preferably, $R_5$ of formula (I) can be C2 alkyl substituted with tolyl.

The method as provided in the present disclosure, wherein when A and B of formula (I) are not bonded, A is H or —OH, and B is H, then $R_5$ is preferably a substituted or unsubstituted phenyl. Wherein $R_5$ can be phenyl substituted with —OH or —$OR_8$, and $R_8$ is C1-C5 alkyl, preferably, $R_5$ can be phenyl substituted with —OH or —O—$CH_3$.

The method as provided in the present disclosure, wherein when A and B of formula (I) are bonded to form a ring, A is O and B is C=O, then $R_5$ preferably is a substituted or unsubstituted phenyl or C2-C5 alkenyl. Wherein $R_5$ can be C2-C5 substituted with phenyl, preferably, $R_5$ can be C2 alkyl substituted with tolyl.

In the present disclosure, the term "halogen" refers to fluorine, chlorine, bromine, iodine and astatine. The term "alkyl" refers to, but not limited to, C1-C5 linear or branched hydrocarbon group; and the examples thereof comprises, but not limited to, methyl, ethyl, n-propyl, iso-propyl, n-butyl, iso-butyl and tort-butyl. The term "alkenyl"

refers to C1-C5 linear or branched hydrocarbon group having at least one double bond such as —CH═CH—CH₃; and the examples thereof comprises, but not limited to, propenyl, propenylidene, allyl and 1,4-butadienyl.

In the present disclosure, the compound represented by the formula (I) preferably is a compound represented by the following formulas (I-1) to (I-5):

However, the compound represented by formula (I) is not limited to the five compounds represented by formulas (I-1) to (I-5).

In the present disclosure, the aforesaid compounds can inhibit β-amyloid aggregation, reduce oxidative stress (such as ROS content), reduce cell death (such as caspase-3), and protect nerves (such as promoting neurite outgrowth); and thus the compounds can treat or effectively delay neurodegenerative diseases related to abnormal β-amyloid aggregation.

In the present disclosure, the aforementioned compounds may be used for various purposes. In addition to the use for preparation of pharmaceutical compositions for treating or delaying abnormal β-amyloid aggregation mediated diseases and inhibiting β-amyloid aggregation, the compounds can also be used for preparation of pharmaceutical compositions for reducing oxidative stress (for example, ROS content), reducing cell death (for example, caspase-3 activity), protecting nerves (for example, promoting neurite outgrowth), and the like.

The pharmaceutical compositions prepared by the present disclosure may include one or more any compounds described above, for example, a compound represented by formula (I) or a compound selected from the group consisting of compounds represented by formula (I-1) to formula (I-5).

The pharmaceutical compositions may further comprise: at least one pharmaceutically accepted carrier, a diluent, or an excipient. The carrier, the diluent, or the diluent must be acceptable, which means they are compatible with main ingredients of the pharmaceutical composition (preferably capable of stabilizing the main ingredient), and are not harmful to target individuals. For example, the compound can be encapsulated into liposome to facilitate delivery and absorption. Alternatively, the compound can be diluted with aqueous suspension, dispersion or solution to facilitate injection. Or, the compound can be produced in a form of a capsule or tablet for storage and carrying.

In the pharmaceutical composition of the present disclosure, the concentration of the aforementioned compounds, such as compounds of formula (I) or formulas (I-1) to (I-5) is not particularly limited and can be adjusted according to actual use such as route of administration, the carrier, the diluent, the excipient, complementary medicines, disorder severity, and the like. A person skilled in the art can adjust the dose to obtain desired curative effect. In one embodiment of the present disclosure, the concentration of aforementioned compounds, such as compounds of formulas (I-1) to (I-5) is in a range from 0.0005 μM to 150 μM, preferably from 0.001 μM to 100 μM, more preferably from 0.05 μM to 50 μM, most preferably from 0.01 μM to 10 μM, based on a total weight of the pharmaceutical composition.

The prepared pharmaceutical composition of the present disclosure can be formulated in a solid or liquid form. When the pharmaceutical composition is in the solid form, solid excipients may include powders, granules, tablets, capsules suppositories, and the like. Pharmaceutical compositions in solid form may further include, but not limited to, solid formulation such as flavoring agents, binders, preservatives, disintegration agents, glidants, and the like. In addition, the liquid excipients used in the pharmaceutical compositions in liquid form may include water, solutions, suspensions, emulsion, and the like. The pharmaceutical compositions in liquid form may further include liquid formulations, for example, but not limited to, coloring agents, flavoring agents, dispersing agents, antibacterial agents, stabilizers, viscosity-increasing agents, and the like.

For example, a powder formulation may be prepared by simply mixing the compound used in the present disclosure with suitable pharmaceutically acceptable excipients such as sucrose, starch and microcrystalline cellulose. A granule formulation may be prepared by mixing the compound used in the present disclosure with suitable pharmaceutically acceptable excipients, and suitable pharmaceutically acceptable binders such as polyvinyl pyrrolidone and hydroxypropyl cellulose, followed by wet granulation method using a solvent, such as water, ethanol, and isopropanol or dry granulation method using compression force. Also, a tablet formulation may be prepared by mixing the granule formulation with suitable pharmaceutically acceptable glidants, such as magnesium stearate, followed by tableting using a tablet machine. Hence, a person skilled in the art can appropriately choose suitable formulation according to his/her needs.

In the present disclosure, the prepared pharmaceutical compositions can be used for treating or delaying abnormal β-amyloid aggregation mediated diseases, inhibiting β-amyloid aggregation, reducing oxidative stress such as ROS content, reducing cell death such as caspase-3 activity, and increasing nerves protection such as neurite outgrowth. Accordingly, the present disclosure also provides a method for treating or delaying abnormal β-amyloid aggregation mediated diseases, inhibiting β-amyloid aggregation, reducing oxidative stress such as ROS content, reducing cell death such as caspase-3 activity, and increasing nerves protection such as neurite outgrowth; the method includes providing a targeting subject and giving the targeting subject the aforementioned pharmaceutical compositions.

The abnormal β-amyloid aggregation mediated diseases is not limited, it may be Alzheimer's disease.

To implement the method according to the present disclosure, the above pharmaceutical composition can be administered via parenteral administering, oral administering, nasal administering, rectal administering, topical administering, or sublingual administering.

The term "parenteral" used herein refers to subcutaneous injection, intradermal injection, intravenous injection, intramuscular injection, intra-articular injection, intraocular injection, intrasternal injection, cerebrospinal injection, intra-lobular or intracranial injection, and any other suitable injection technique. The pharmaceutical compositions for oral administration may be in any formulation acceptable for oral administration including granules, capsules, tablets, emulsions, aqueous suspensions, dispersing agents, and solutions.

The term "treat" used herein refers to achieving the desired medical and physical effect. The effect may be preventing or partially preventing a disease, a prophylactic method for a symptom or condition thereof, completely or partially cure of disease, or a therapy for symptoms or adverse reactions caused by a disease. The term "treatment" used herein encompasses the treatment for mammals, especially for human diseases, and includes prevention of a disease which is predisposed but not diagnosed, or alleviating a disease which means a use for alleviating a disease and/or the symptoms thereof.

The term "delay", "inhibit", "decrease", or "reduce" used herein refers to a case that the pharmaceutical composition of the present disclosure is applied to a targeting subject suffering from abnormal β-amyloid aggregation mediated disease, having symptoms or disorder of a disease, or having a tendency of development of a disease in order to achieve cure, mitigation, alleviation, improvement, or recovery of the tendency of the symptoms.

Other objects, advantages, and novel features of the present disclosure will become more apparent from the following detailed description when taken in conjunction with the accompanying drawings.

DETAILED DESCRIPTION OF THE PREFERRED EMBODIMENT

[Compounds]

Please refer to Table 1. Table 1 shows the structure, chemical formula, and molecular weight of compounds tested in the following experiments, namely compound (I-1), compound (I-2), compound (I-3), compound (I-4), and compound (I-5). However, the test compounds are not limited to five compounds described above.

TABLE 1

| Compound | Structure | Chemical Formula | Molecular Weight (g/mole) |
|---|---|---|---|
| Compound (I-1) | | $C_{16}H_{13}O_3Br$ | 333.18 |

TABLE 1-continued

| Compound | Structure | Chemical Formula | Molecular Weight (g/mole) |
|---|---|---|---|
| Compound (I-2) | | $C_{16}H_{14}O_3$ | 254.28 |
| Compound (I-3) | | $C_{19}H_{14}O_4$ | 306.31 |
| Compound (I-4) | | $C_{16}H_{14}O_4$ | 270.28 |
| Compound (I-5) | | $C_{16}H_{10}O_4$ | 266.25 |

The following experiments tested not only the five compounds described above but also licochalcone A and curcumin. Since these two compounds are known to have potential for treating Alzheimer's disease, they are used as positive control group in the following experiments.

[Solubility Test for Compounds]

This experiment was to test the solubility of compound (I-1), compound (I-2), compound (I-3), compound (I-4), and compound (I-5) in cell culture medium. After vortex mixing and centrifugation for five minutes at 13,000 g, the compounds were completely soluble in the cell culture medium up to 100 μM.

[Cytotoxicity Test for Compounds]

This experiment was to test the toxicity of compounds (I-1), (I-2), (I-3), (I-4), and (I-5) to un-induced Tet-On Aβ-GFP Ftp-In 293 and SH-SY5Y cells. Un-induced Tet-On Aβ-GFP Flp-In 293 and SH-SY5Y cells were treated with compounds (I-1), (I-2), (I-3), (I-4), and (I-5) in different concentrations from 0.1 to 100 μM for 24 hours, followed by conducting MTT assay to test the cytotoxicity of the compounds. The experiment also tested the cytotoxicity of licochalcone A (0.1-100 μM) and curcumin (1-10 μM) to the un-induced Tet-On Aβ-GFP Flp-In 293 and SH-SY5Y cells. In the experiment, the relative cellular survival rate of untreated cells was 100%, the half maximal inhibitory concentration ($IC_{50}$) of each compound was calculated by using interpolation, and the sample number of each group was n=3.

Figure 1A:
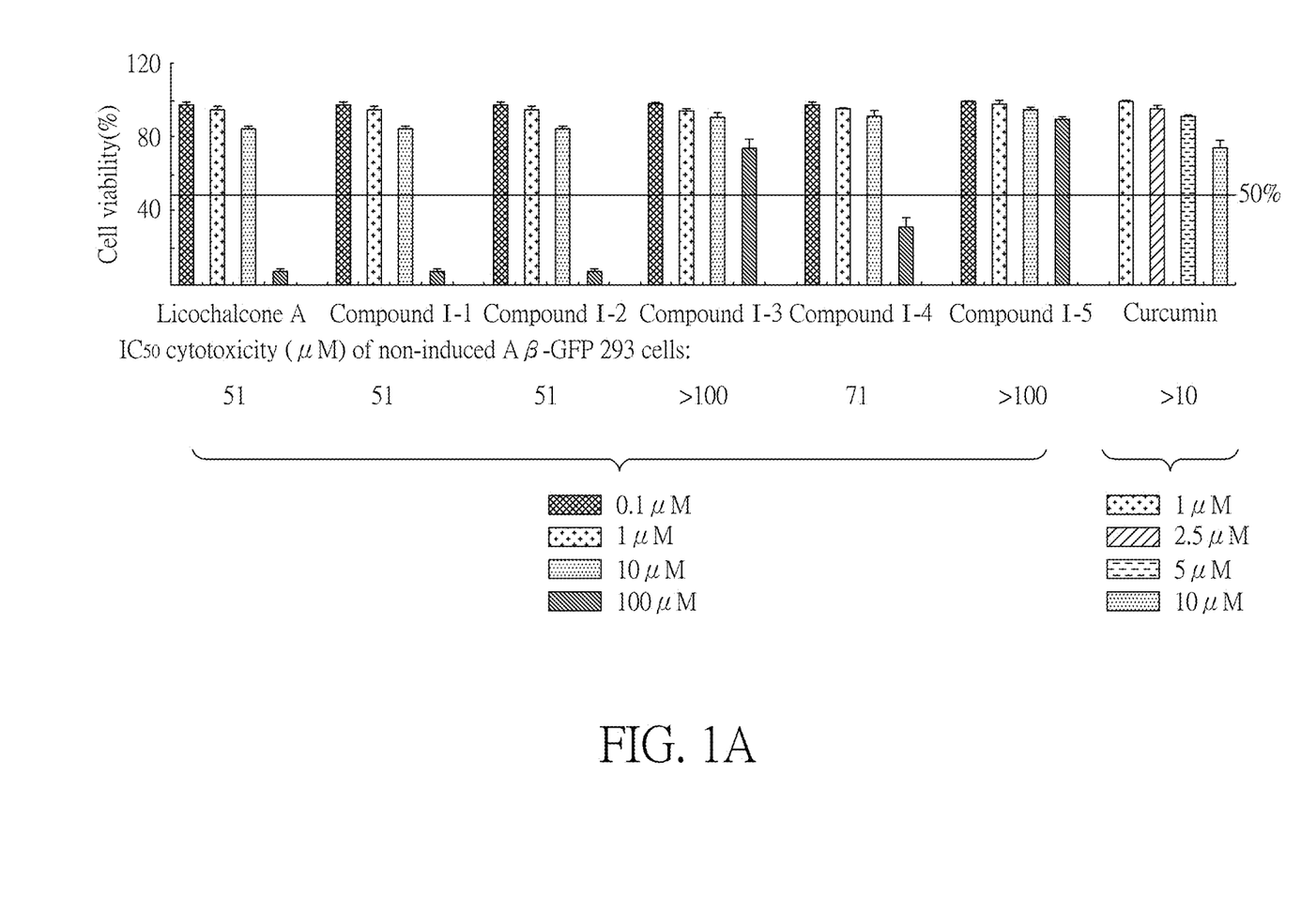
FIG. 1A shows the $IC_{50}$ cytotoxicity of the un-induced Tet-On Aβ-GFP Flp-In human embryonic kidney 293 cells treated with the test compounds in one preferred embodiment of the present disclosure.
Figure 1B:
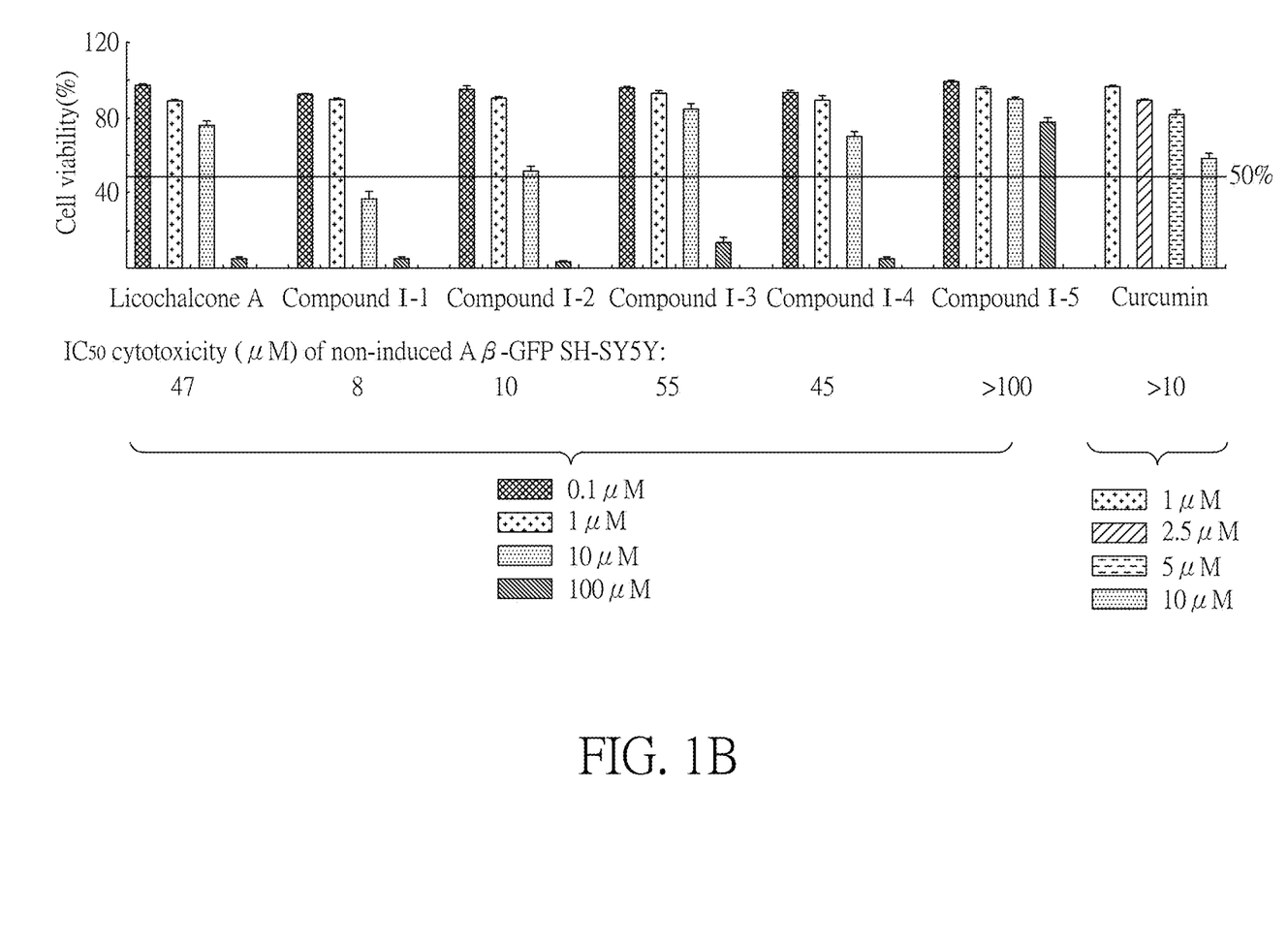
FIG. 1B shows the $IC_{50}$ cytotoxicity of the un-induced Tet-On Aβ-GFP human neuroblastoma SH-SY5Y cells treated with the test compounds in one preferred embodiment of the present disclosure.

Please refer to FIGS. 1A and 1B. FIG. 1A shows the cytotoxicity of un-induced. Tet-On Aβ-GFP Flp-In 293 cells treated with the aforementioned compounds, and FIG. 1B shows the cytotoxicity of un-induced Tet-On Aβ-GFP SH-SY5Y cells treated with the aforementioned compounds.

As shown in FIG. 1A and FIG. 1B, the cytotoxicity of compound (I-5) ($IC_{50}$>100 μM) is much lower than that of licochalcone A ($IC_{50}$=47-51 μM) and curcumin ($IC_{50}$>10 μM), and the cytotoxicity of compound (I-1) ($IC_{50}$=8-51 μM), compound (I-2) ($IC_{50}$=10-51 μM), compound (I-3) ($IC_{50}$=55->100 μM), and compound (I-4) ($IC_{50}$=45-71 μM) are similar to that of licochalcone A and curcumin. It demonstrates that the cytotoxicity of the test compounds is similar to or lower than the cytotoxicity of licochalcone A and curcumin, which are known to have potential for treating neurodegenerative diseases related to abnormal β-amyloid aggregation such as Alzheimer's disease.

[Inhibition of Abnormal β-Amyloid Aggregation Test]

In the experiment, Tet-On Aβ-GFP Flp-In human embryonic kidney 293 cells were used as a screen platform to test whether compounds (I-1), (I-2), (I-3), (I-4), and (I-5) can inhibit Aβ aggregation. GFP fluorescence was used to reflect Aβ aggregation status as Aβ aggregated to cause the fused GFP misfolded, and thus cause the reduction of fluorescence on Aβ-GFP expressing cells. Inhibition of Aβ aggregation may improve GFP misfolding and lead to increased fluorescence on Aβ-GFP expressing cells. After Tet-On Aβ-GFP Flp-In 293 cells were cultured for 24 hours, the cells were treated with different concentrations of compounds (I-1), (I-2), (I-3), (I-4), and (I-5) for 8 hours. Then doxycycline (Dox) (2 μg/mL) was added to the cells for 64 hours to induce the Aβ-GFP expression, and GFP fluorescence was assessed by a high-content analysis (HCA) system (ImageXpressMICRO, available from Molecular Devices). The experiment also tested the inhibition effect of Aβ aggregation by curcumin (1-10 μM) and licochalcone A (0.001-100 μM). In the experiment, the amount of fluorescence measured in the untreated group (untreated with compounds) was 100%, and the sample number of each group was n=3.

Figure 2A:
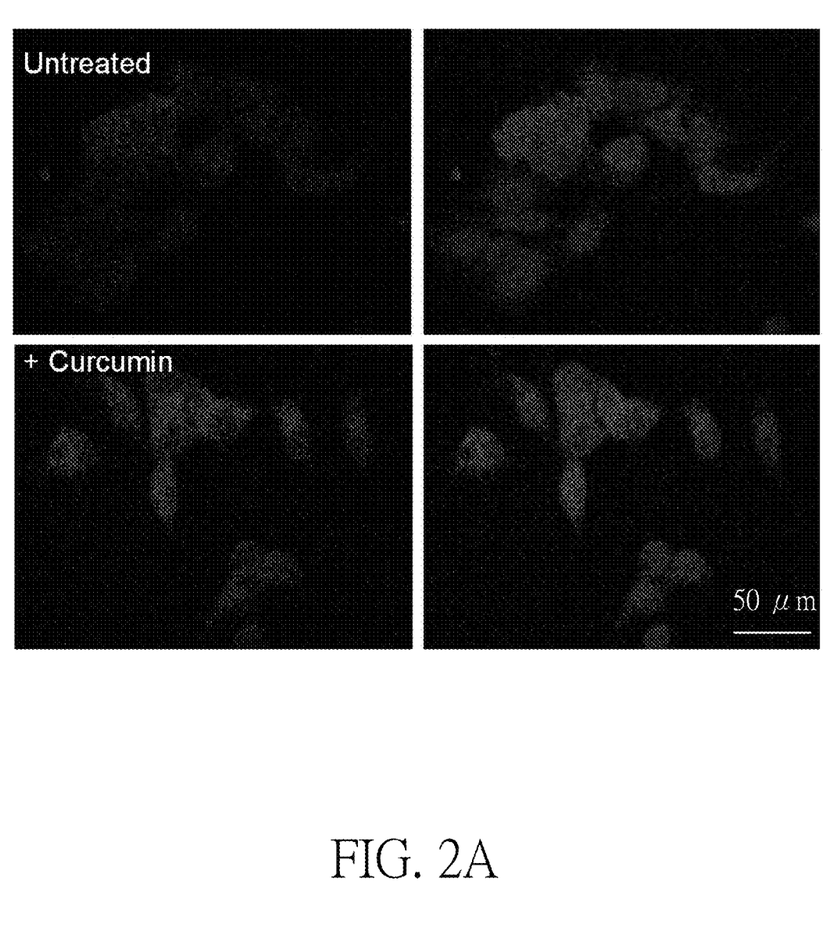
FIG. 2A shows the images of GFP fluorescence of the induced Tet-On Aβ-GFP Flp-In 293 cells treated with curcumin as a positive control group in one preferred embodiment of the present disclosure.
Figure 2B:
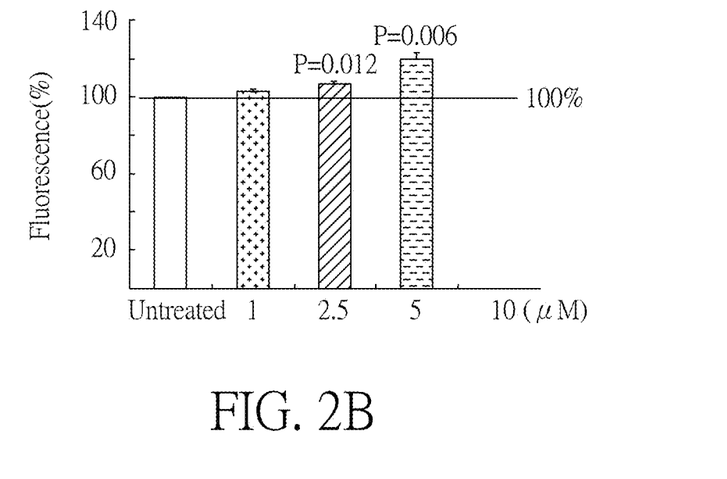
FIG. 2B shows the amount of GFP fluorescence of the induced Tet-On Aβ-GFP Flp-In 293 cells treated with curcumin as a positive control group in one preferred embodiment of the present disclosure.
Figure 2C:
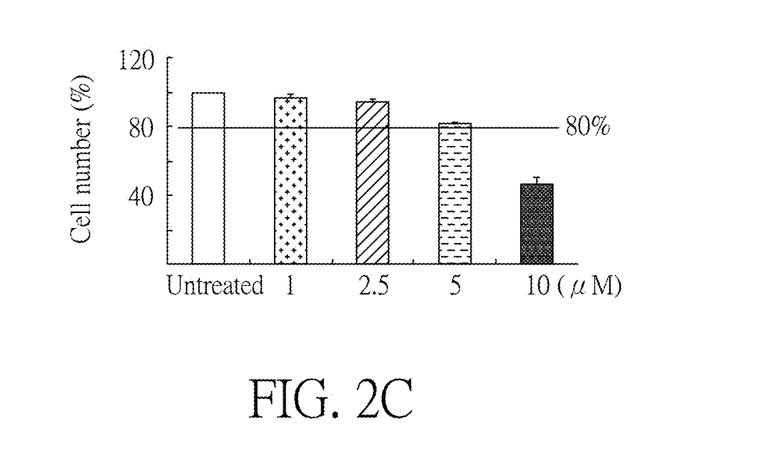
FIG. 2C shows the cell number of the induced Tet-On Aβ-GFP Flp-In 293 cells treated with curcumin as a positive control group in one preferred embodiment of the present disclosure.

Please refer to FIG. 2A to 2C. FIG. 2A shows the images of GFP fluorescence of Tet-On Aβ-GFP Flp-In 293 cells treated or untreated with curcumin (5 μM). FIG. 2B shows the amount of GFP fluorescence of Tet-On Aβ-GFP Ftp-In 293 cells treated with curcumin (1-10 μM). FIG. 2C shows the cell number of Tet-On Aβ-GFP Flp-In 293 cells treated with curcumin (1-10 μM). As shown in FIG. 2A and FIG. 2B, when the concentrations of curcumin were 2.5 μM and 5 μM, GFP fluorescence was increased significantly, namely Aβ aggregation was inhibited significantly (treated 107-120% vs. untreated 100%, P=0.012-0.006). As shown in FIG. 2C, the cell numbers of Tet-On Aβ-GFP Flp-In 293 cells treated with 2.5 μM and 5 μM curcumin were more than 80% of untreated cells.

Figure 3A:
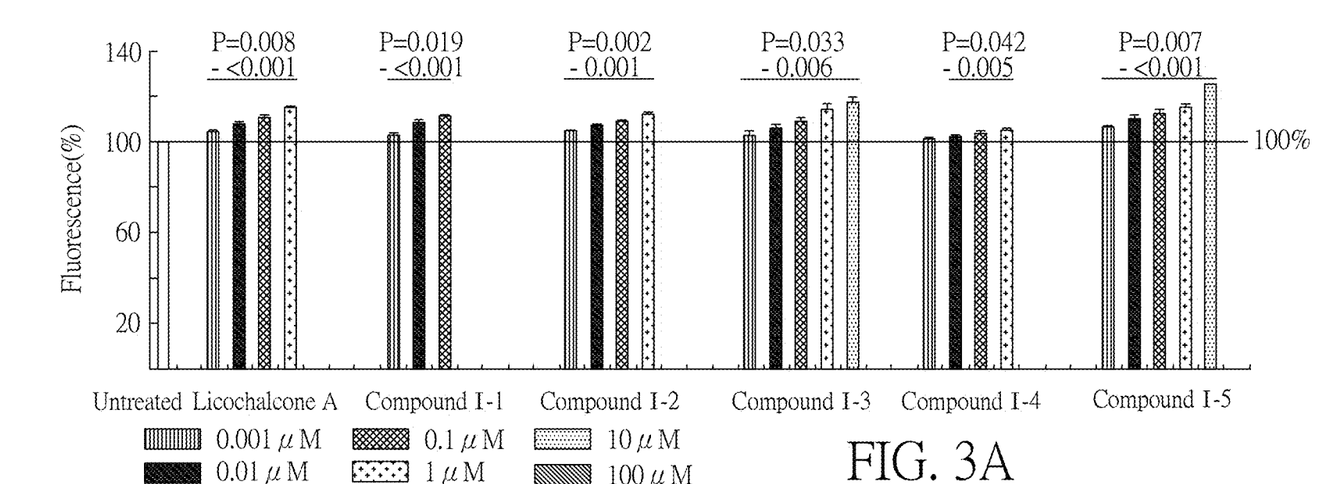
FIG. 3A shows the amount of GFP of the induced Tet-On Aβ-GFP Flp-In 293 cells treated with the test compounds in one preferred embodiment of the present disclosure.
Figure 3B:
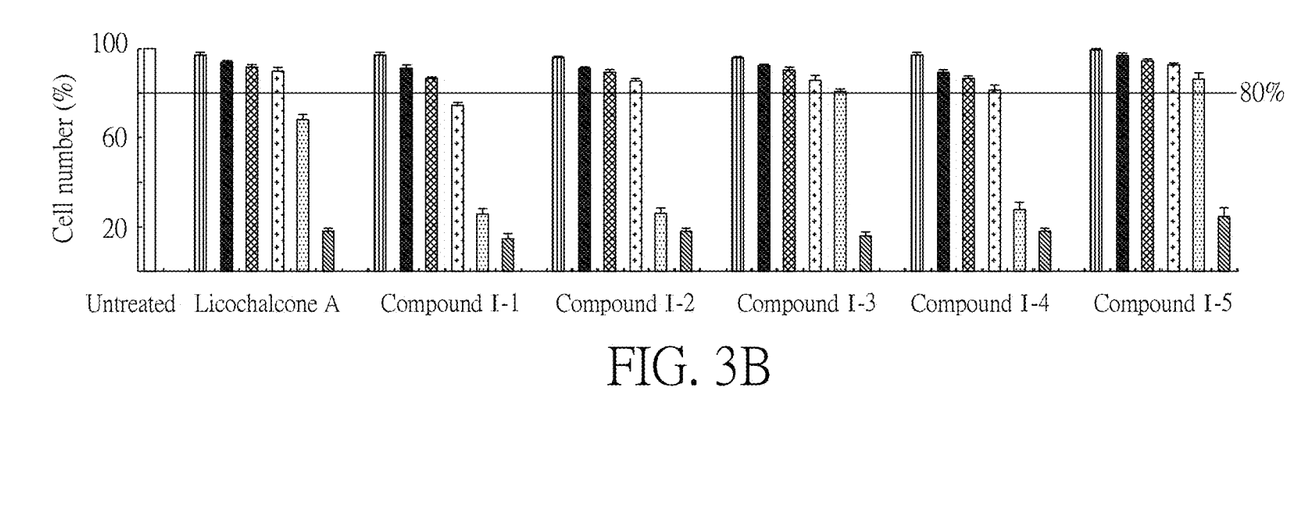
FIG. 3B shows the cell number of the induced Tet-On Aβ-GFP Flp-In 293 cells treated with the test compounds in one preferred embodiment of the present disclosure.
Figure 3C:
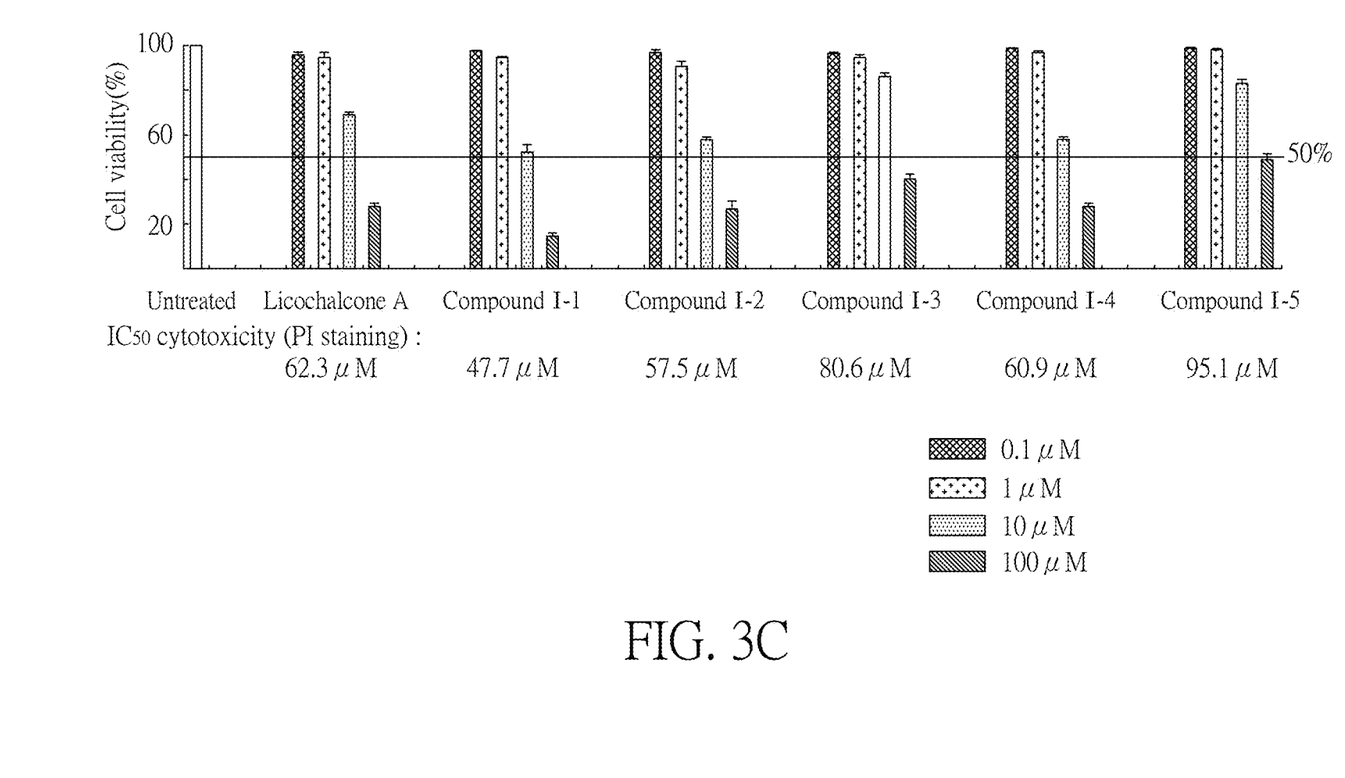
FIG. 3C shows the $IC_{50}$ cytotoxicity of the induced Tet-On Aβ-GFP Flp-In 293 cells treated with the test compounds according to the number of viable cells stained with propidium iodide (PI) in one preferred embodiment of the present disclosure.

See FIG. 3A to 3C. FIG. 3A shows the amount of GFP fluorescence of Tet-On Aβ-GFP Flp-In 293 cells treated with compound (I-1), compound (I-2), compound (I-3), compound (I-4), compound (I-5), and licochalcone A (0.001-100 μM). FIG. 3B shows the number of viable Tet-On Aβ-GFP Flp-In 293 cells treated with aforementioned compounds. FIG. 3C shows the $IC_{50}$ cytotoxicity of the Tet-On Aβ-GFP Ftp-In 293 cells treated with the aforementioned compounds stained with propidium iodide (PI) and analyzed by a flow cytometer.

As shown in 3A and 3B, when the cell survival rate was more than 80%, the GFP fluorescence of Tet-On Aβ-GFP Flp-In 293 cells treated with different concentration of compounds increased significantly compared to untreated groups, namely Aβ aggregation was inhibited significantly. In details, the GFP fluorescence of Tet-On Aβ-GFP Flp-In 293 cells treated with compound (I-1) (0.001-0.1 μM) increased to 103-111% (P=0.019-<0.001), compound (I-2) (0.001-1 μM) increased to 105-112% (P=0.002-0.001), compound (I-3) (0.001-10 μM) increased to 103-117% (P=0.033-0.006), compound (I-4) (0.01-1 μM) increased to 102-105% (P=0.042-0.005), compound (I-5) (0.001-10 μM) increased to 107-125% (P=0.007-<0.001), and licochalcone A (0.001-1 μM) increased to 105-115% (P=0.008-<0.001). As shown in FIG. 3C, cytotoxicity of compound (I-3) ($IC_{50}$=80.6 μM) and compound (I-5) ($IC_{50}$=95.1 μM) were less than that of licochalcone A ($IC_{50}$=62.3 μM) as positive control group; also, cytotoxicity of compound (I-1) ($IC_{50}$=47.7 μM), compound (I-2) ($IC_{50}$=57.5 μM), and compound (I-4) ($IC_{50}$=60.9 μM) were higher than or similar to that of licochalcone A.

According to results shown in from FIG. 2A to 3C, it is demonstrated that the test compounds are like compounds known to have potential for treating neurodegenerative diseases related to abnormal β-amyloid aggregation such as Alzheimer's disease, and can inhibit Aβ aggregation. Furthermore, the cytotoxicity of the test compounds is lower than or similar to that of compounds known to have potential for treating neurodegenerative diseases related to abnormal β-amyloid aggregation such as Alzheimer's disease. Wherein, compound (I-3) and compound (I-5) have wider range of concentrations for inhibiting Aβ aggregation than other compounds and compounds used as positive control group do. As a result, the test compounds may replace the compounds known to have potential for treating neurodegenerative diseases related to abnormal β-amyloid aggregation such as Alzheimer's disease to be new or better inhibitors of Aβ aggregation.

[Reduction of Oxidative Stress, Such as ROS Content and Cell Death, Such as Caspase-3 Activity Test for Compounds]

Since Aβ deposition increases oxidative stress and leads to nerve cell death, the purpose of this experiment is to see whether the compound (I-2) (1 μM), compound (I-3) (1-10 μM), compound (I-4) (1 μM), and compound (I-5) (1-10 μM) can reduce the ROS content and caspase-3 activity of Tet-On Aβ-GFP Flp-In 293 cells. In the experiment, two positive control groups, licochalcone A (1 μM) and curcumin (5 μM), were also included to test the ROS content and caspase-3 activity of Tet-On Aβ-GFP Flp-In 293 cells. In this experiment, the relative ROS content and caspase-3 activity of un-induced (untreated with doxycycline) cells were determined to be 100%, and the sample number of each group was n=3.

Figure 4:
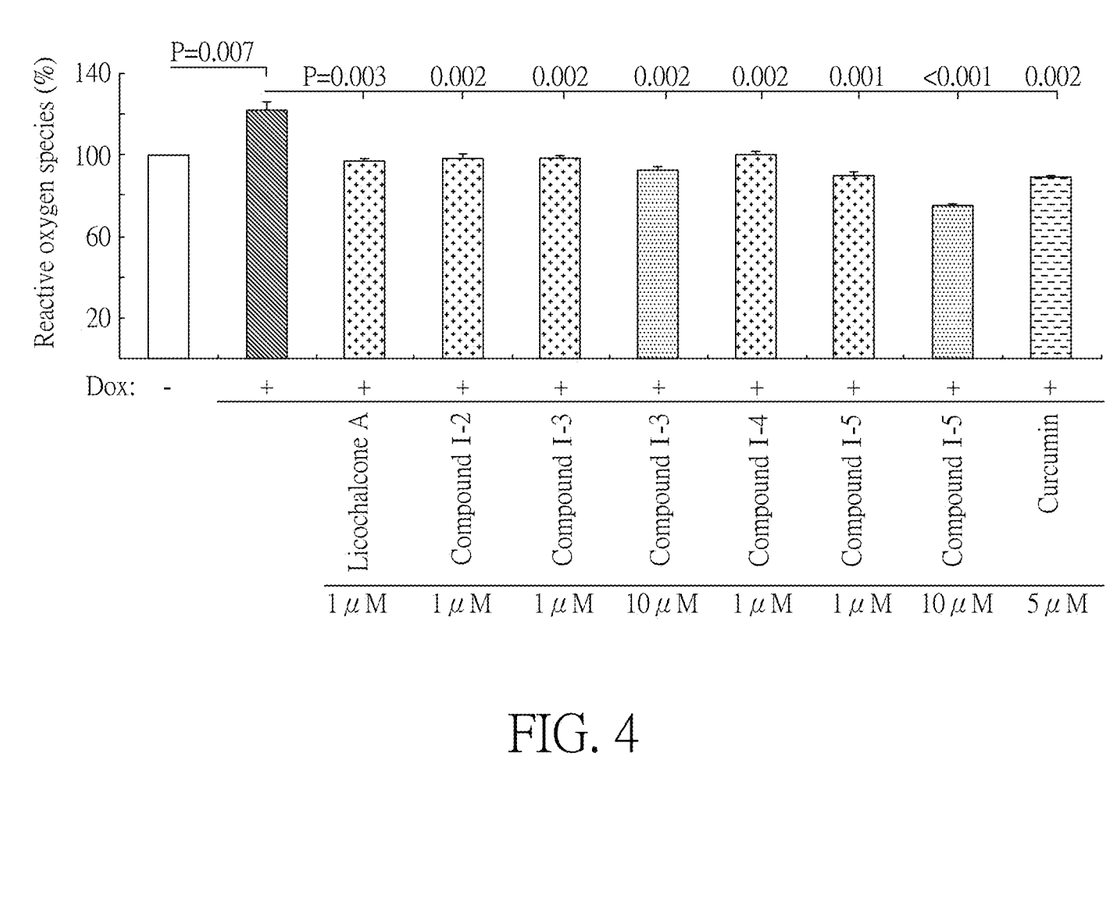
FIG. 4 shows the ROS content of the induced Tet-On Aβ-GFP Flp-In 293 cells treated with the test compounds in one preferred embodiment of the present disclosure.
Figure 5:
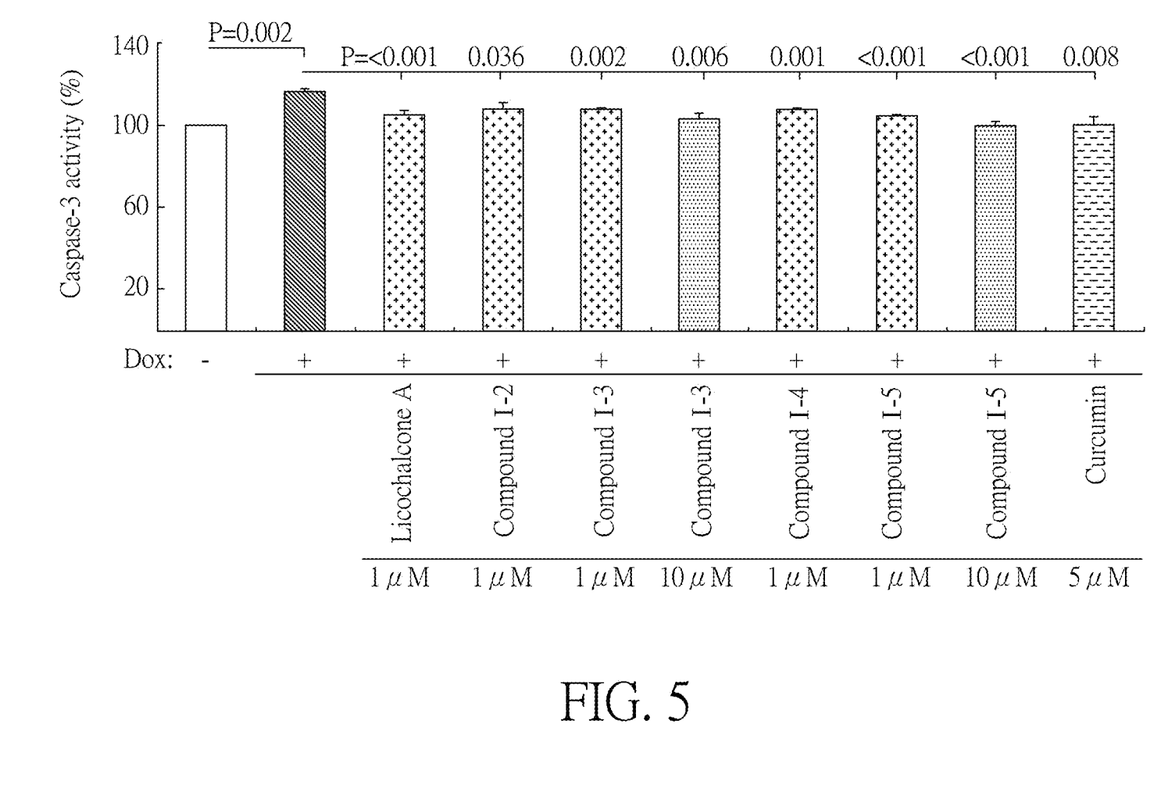
FIG. 5 shows the caspase-3 activity of induced Tet-On Aβ-GFP Flp-In 293 cells treated with the test compounds in one preferred embodiment of the present disclosure.

Please refer to FIGS. 4 and 5. FIG. 4 shows the ROS content of Tet-On Flp-In 293 cells treated with compounds (I-2), (I-3), (I-4), (I-5), licochalcone A, and curcumin. FIG. 5 shows the caspase-3 activity of Tet-On Aβ-GFP Flp-In 293 cells treated with above compounds. As shown in FIG. 4, the ROS content was significantly increased (122% vs. 100%, P=0.007) after induction of Aβ-GET expression compared to the un-induced group. The ROS content of Tet-On Aβ-GFP Flp-In 293 cells treated with compounds (I-2), (I-3), (I-4), (I-5), licochalcone A, and curcumin were significantly lower than that of untreated group (75-100% vs. 122%, P=0.003-<0.001). As shown in FIG. 5, the caspase-3 activity of Tet-On Aβ-GFP Flp-In 293 cells was significantly increased (116% vs. 100%, P=0.002) after induction of Aβ-GFP expression compared to the un-induced group. The caspase-3 activity of Tet-On Aβ-GYP Flp-In 293 cells treated with compounds (I-2), (I-3), (I-4), (I-5), licochalcone A, and curcumin were significantly lower than that of untreated group (100-107% vs. 116%, P=0.036-<0.001). As a result, the test compounds can reduce oxidative stress (such as ROS content) and apoptosis (such as caspase-3 activity) as the compounds known to have potential for treating neurodegenerative diseases related to abnormal β-amyloid aggregation such as Alzheimer's disease.

[Nerve Protection, Such as Promoting Neurite Outgrowth Test for Compounds]

Human neuroblastoma SH-SY5Y cell clone with Tet-On Aβ-GFP expression were used to test whether compounds (I-2), (I-3), (I-4), and (I-5) can protect nerves such as promoting neurite outgrowth, Tet-On Aβ-GFP SH-SY5Y cells were plated into 24-well plates, added with retinoic acid (RA, 10 μM) to induce neuron differentiation, grown for 24 hours, and then treated with different concentrations of compound (I-2) (1 μM), compound (I-3) (1-10 μM), compound (I-4) (1 μM), and compound (I-5) (1-10 μM) for 8 hours. Then the Tet-On Aβ-GFP SH-SY5Y cells were treated with doxycycline (2 ng/mL) for six days. Neurite outgrowth was assessed after TUBB3 immunostaining, and examined with the RCA system. In this experiment, licochalcone A (1 μM) and curcumin (5 μM) in the positive control group were also tested for the effect of nerve protection such as promoting neurite outgrowth. Furthermore, the relative neurite outgrowth of un-induced group (untreated with doxycycline) is determined as 100%, and the sample number of each group was n=3.

Figure 6A:
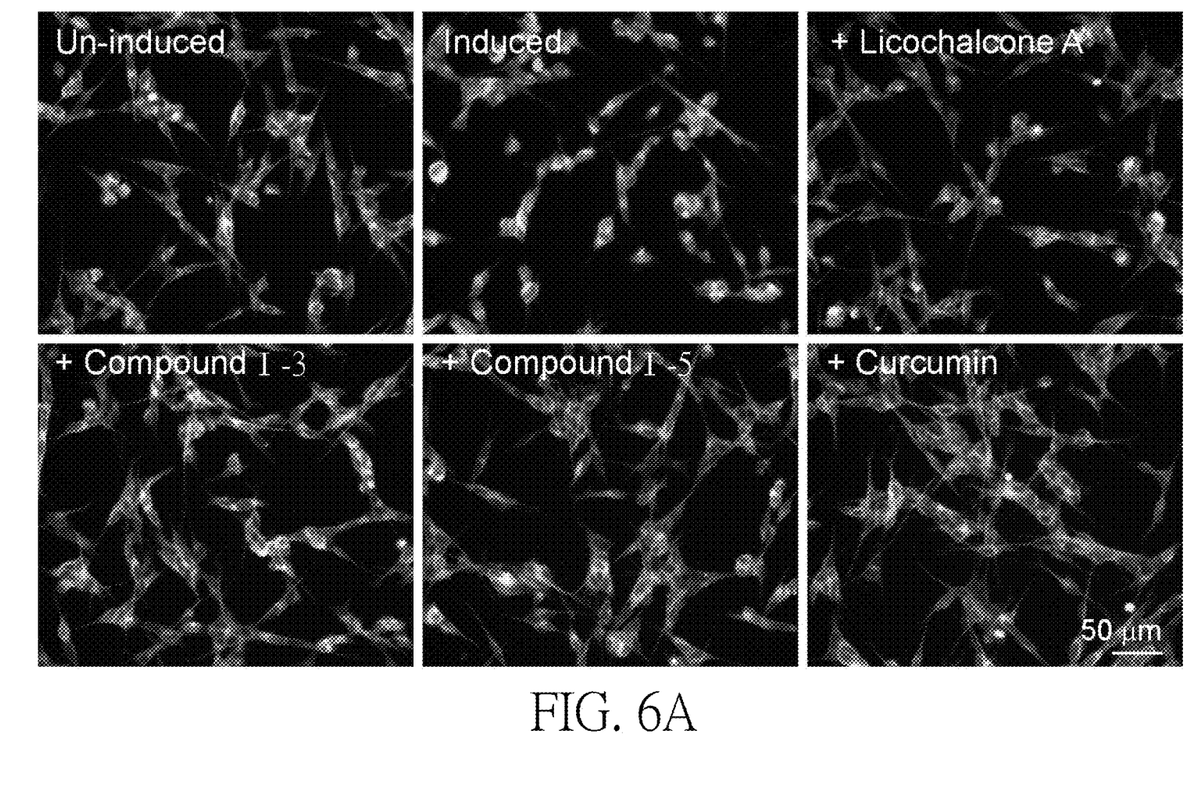
FIG. 6A shows staining images of the neurite outgrowth of the induced Tet-On Aβ-GFP SH-SY5Y cells treated with the test compounds in one preferred embodiment of the present disclosure.
Figure 6B:
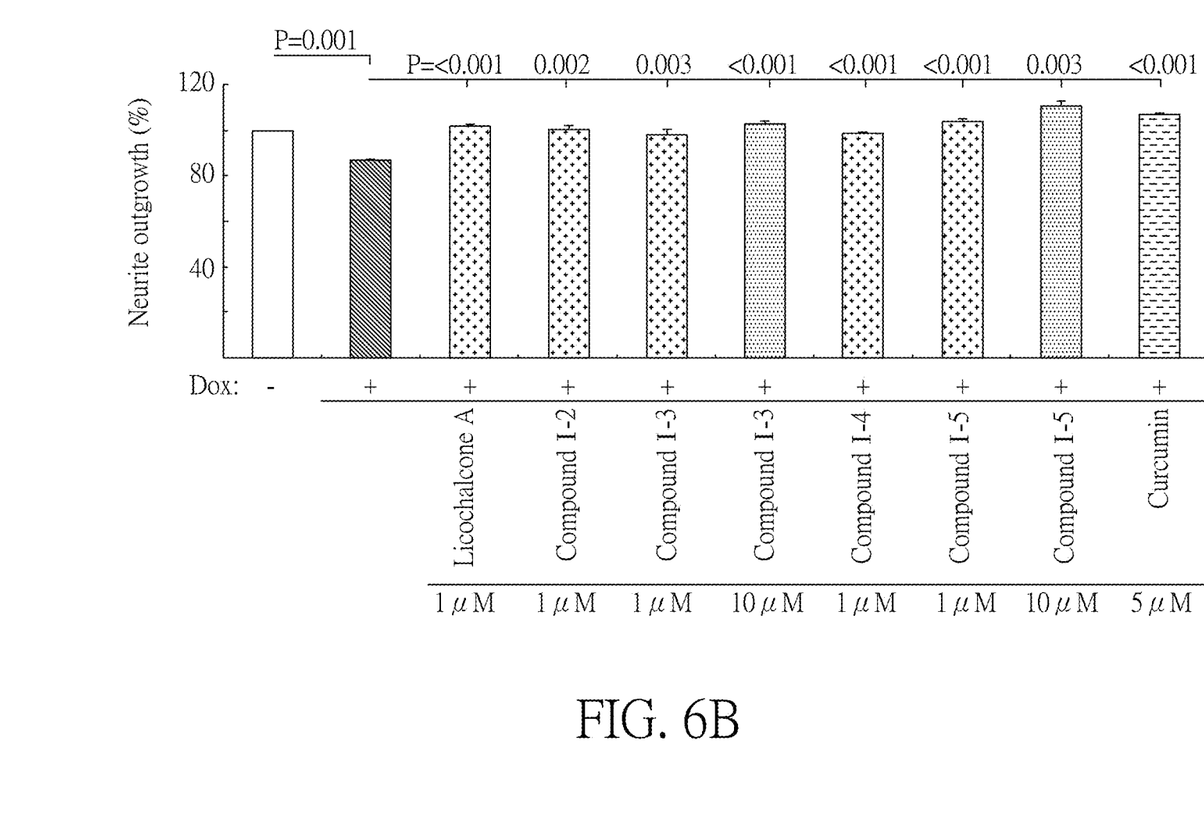
FIG. 6B shows the amount of neurite outgrowth of induced Tet-On Aβ-GYP SH-SY5Y cells treated with the test compounds in one preferred embodiment of the present disclosure.

See FIG. 6A to 6C. FIG. 6A shows the fluorescence images of neurite outgrowth of Tet-On Aβ-GFP SH-SY5Y cells treated with compound (I-3), compound (I-5), licochalcone A (1 μM) and curcumin (5 μM). FIG. 6B shows the amount of neurite outgrowth of Tet-On Aβ-GFP SH-SY5Y cells treated with compound (I-2) (1 μM), compound (I-3)

Figure 6C:
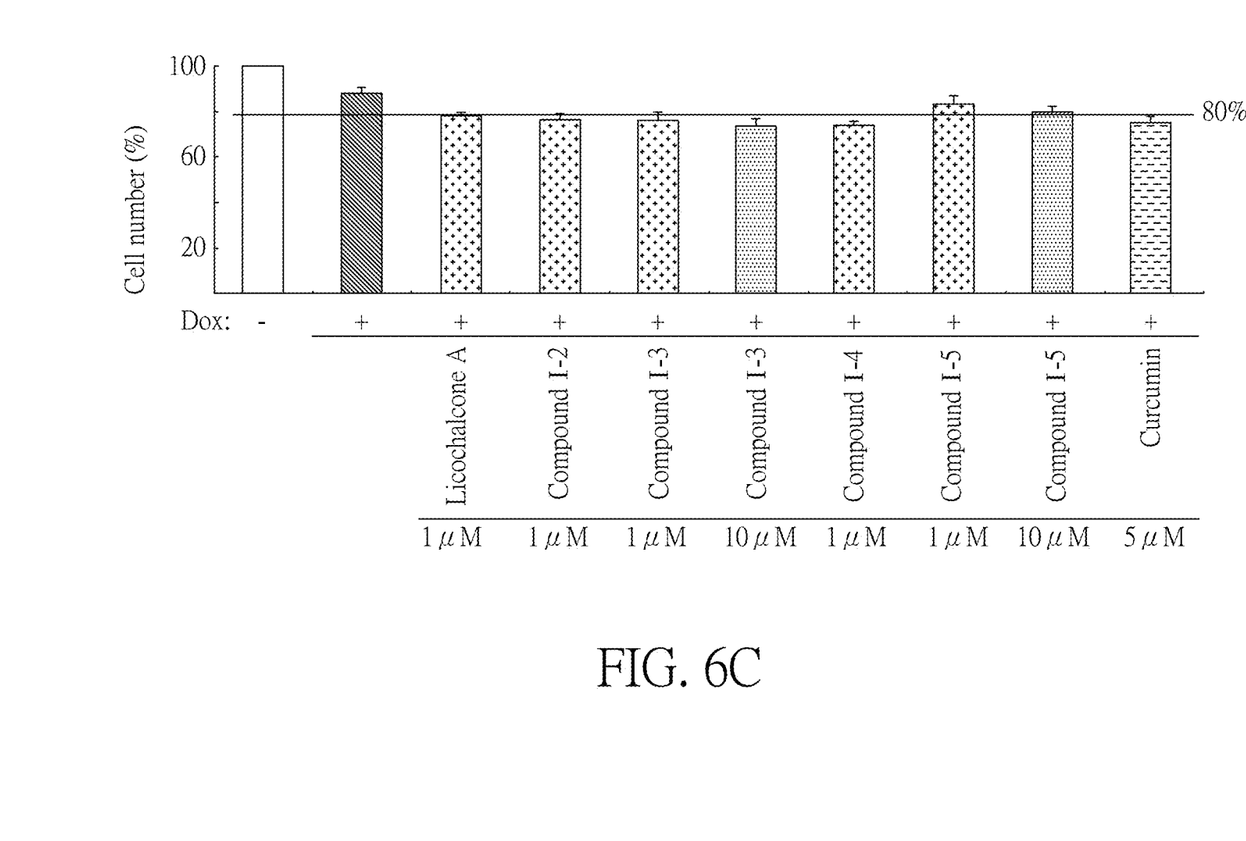
FIG. 6C shows the cell number of the induced Tet-On Aβ-GFP SH-SY5Y cells treated with the test compounds in one preferred embodiment of the present disclosure.

(1-10 μM), compound (I-4) (1 μM), compound (I-5) (1-10 μM), licochalcone A (1 μM) and curcumin (5 μM). FIG. 6C shows the survival number of Tet-On Aβ-GFP SH-SY5Y cells treated with above compounds. As shown in FIG. 6A and FIG. 6B, the neurite outgrowth of the group, which was induced Aβ-GFP expression, was significantly decreased (87% vs. 100%, P=0.001) in comparison with the un-induced group. Compared to un-induced group, the amount of the neurite outgrowth of Tet-On Aβ-GFP SH-SY5Y cells treated with compound (I-2), compound (I-3), compound (I-4), compound (I-5), licochalcone A, and curcumin were significantly increased (110-98% vs. 87%, P=0.003-<0.001). As shown in FIG. 6C, the survival number of Tet-On Aβ-GFP SH-SY5Y cells treated with compound (I-2), compound (I-3), compound (I-4), and compound (I-5) was similar to that of licochalcone A and curcumin in positive control groups.

The results shown in FIG. 6A to 6C demonstrated that the test compounds can promote neurite outgrowth and protect nerves as the compounds known to have potential for treating neurodegenerative diseases related to abnormal β-amyloid aggregation such as Alzheimer's disease.

In the present disclosure, a group of novel compounds was tested; also, Flp-In 293 and SH-SY5Y cells with inducible Aβ-GFP expression were used as a platform to screen the compounds having potential to inhibit abnormal β-amyloid aggregation. When the tested compounds can inhibit or retard abnormal β-amyloid aggregation, the GFP fluorescence of cells will be enhanced. All the tested compounds of the present disclosure enhanced the green fluorescence in Aβ-GFP expressing cells, namely all the tested compounds inhibited or retarded β-amyloid aggregation. In addition, all the tested compounds of the present disclosure can reduce oxidative stress and protect nerves (such as promoting neurite outgrowth). The results demonstrate that the tested novel compounds can inhibit β-amyloid aggregation and protect nerves, and thus can be used to treat or delay neurodegenerative diseases related to abnormal β-amyloid aggregation such as Alzheimer's disease.

Although the present disclosure has been explained in relation to its preferred embodiment, it is to be understood that many other possible modifications and variations can be made without departing from the spirit and scope of the invention as hereinafter claimed.

What is claimed is:

1. A method for treating a β-amyloid aggregation mediated disease, comprising:
    administering a pharmaceutical composition comprising a compound represented by the following formula (I-5) to a subject in need of treatment for the β-amyloid aggregation mediated disease,

(I-5)

2. The method as claimed in claim 1, wherein a concentration of the compound represented by the formula (I-5) is in a range from 0.0005 μM to 150 μM based on a total weight of the pharmaceutical composition.

3. The method as claimed in claim 1, wherein the pharmaceutical composition further comprises: at least one pharmaceutically acceptable carrier, a diluent, or an excipient.

4. The method as claimed in claim 1, wherein the β-amyloid aggregation mediated disease is Alzheimer's disease.

5. A method for inhibiting β-amyloid aggregation in a subject in need of such inhibition, comprising:
    administering a pharmaceutical composition comprising a compound represented by the following formula (I-5) to the subject, (I-5)

6. The method as claimed in claim 5, wherein a concentration of the compound represented by the formula (I-5) is in a range from 0.0005 μM to 150 μM based on a total weight of the pharmaceutical composition.

7. The method as claimed in claim 5, wherein the pharmaceutical composition further comprises: at least one pharmaceutically acceptable carrier, a diluent, or an excipient.

* * * * *